(12) United States Patent
LeGrow et al.

(10) Patent No.: US 6,228,380 B1
(45) Date of Patent: May 8, 2001

(54) DELIVERY OF HYDROXY CARBOXYLIC ACIDS

(75) Inventors: Gary E. LeGrow, Newberry; W. Leonard Terry, Jr., Gainesville, both of FL (US)

(73) Assignee: Archimica (Florida) Inc., Gainesville, FL (US)

(*) Notice: Subject to any disclaimer, the term of this patent is extended or adjusted under 35 U.S.C. 154(b) by 0 days.

(21) Appl. No.: 09/614,581

(22) Filed: Jul. 12, 2000

Related U.S. Application Data

(60) Division of application No. 09/148,675, filed on Sep. 4, 1998, which is a continuation-in-part of application No. 09/041,173, filed on Mar. 12, 1998, now abandoned.

(51) Int. Cl.$^7$ ............................. A61K 6/00; A61K 7/00; A61K 31/74
(52) U.S. Cl. ........................................ 424/401; 424/78.03
(58) Field of Search .................. 424/401, 78.03

(56) References Cited

U.S. PATENT DOCUMENTS

| | | | |
|---|---|---|---|
| 2,486,993 | 11/1949 | Sowa | 260/78.3 |
| 2,584,340 | 2/1952 | Goodwin et al. | 260/45.4 |
| 5,032,406 | 7/1991 | Dansereau et al. | 424/472 |
| 5,229,131 | 7/1993 | Amidon et al. | 424/451 |
| 5,334,372 | 8/1994 | Kawamata et al. | 424/78.03 |
| 5,374,759 | * 12/1994 | Imperante | 556/437 |
| 5,420,106 | 5/1995 | Parab | 514/2 |
| 5,439,689 | 8/1995 | Hendrickson et al. | 424/490 |
| 5,500,227 | 3/1996 | Oshlack et al. | 424/476 |
| 5,576,022 | 11/1996 | Yang et al. | 424/472 |
| 5,690,947 | 11/1997 | Habif et al. | 424/401 |
| 5,714,155 | 2/1998 | De Lacharriere et al. | 424/401 |
| 5,716,625 | 2/1998 | Hahn et al. | 424/401 |

FOREIGN PATENT DOCUMENTS

| | | |
|---|---|---|
| 2167754 | 6/1986 | (GB) . |
| 197708 | 4/1975 | (SU) ............... A61K/31/69 |
| 0756810 | 6/1979 | (SU) . |

OTHER PUBLICATIONS

Market View, "The U.S. Cosmetics Industry" Special Report AHA Consumer Products 1990 through 1993. http://www.thriveonline.com/42'@@62AH9wYA2@Hgbb2a/thrive/health/skinsave.intro.html Jul. 9, 1997.

Niebling, Genetic Engineering News, Biotech & Drug Firms Claim Territory in Cosmeceutics, Apr. 1, 1996.

Hahn, DCI, A New Line of Defense Against Aging: "Breaking the Irritation Barrier," Jan. 1998.

DCI Keeping Posted, "Next Generation of Skin Care for Aging Skin," p.6, Apr. 1997.

Foltz et al., Chem. Abs. 67:78733 Reactions of labile trimethylsilyl derivatives with fluorocarbons in a gas chromatograph–mass spectrometer system (1967).

* cited by examiner

Primary Examiner—Thurman K. Page
Assistant Examiner—S. Howard
(74) Attorney, Agent, or Firm—Hedman & Costigan P.C

(57) ABSTRACT

The present invention provides greater than 99% pure bis (triorganosilyl)hydroxycarboxylates of the general formulae:

$$R_3SiO\text{—}CHR^1\text{—}COO\text{—}SiR_3$$

$$R_3SiO\text{—}CHR^1\text{—}R^2COO\text{—}SiR_3$$

wherein each R is independently a monovalent straight or branched chain alkyl or alkenyl group having from 1 to about 6 carbon atoms, or an aryl group, $R^1$ may be hydrogen, a monovalent straight or branched chain alkyl group having from 1 to about 18 carbon atoms, or an aryl group, and $R^2$ is a divalent straight or branched chain alkyl group having from 1 to about 18 carbon atoms, an aryl group, or a straight or branched chain alkaryl group having from 7 to about 18 carbon atoms; a process for producing the bis(trimethylsilyl) hydroxycarboxylates comprising the trimethylsilylation with hexamethyldisilazane of the corresponding hydroxy carboxylic acids; cosmetic formulation comprising the greater than 99% pure bis(trimethylsilyl) hydroxycarboxylates dissolved in aprotic media; and a method of delivering hydroxycarboxylic acids to the epidermis without apparent irritation or inflammation of the epidermis or stratum corneum.

9 Claims, 1 Drawing Sheet

(1 of 1 Drawing Sheet(s) Filed in Color)

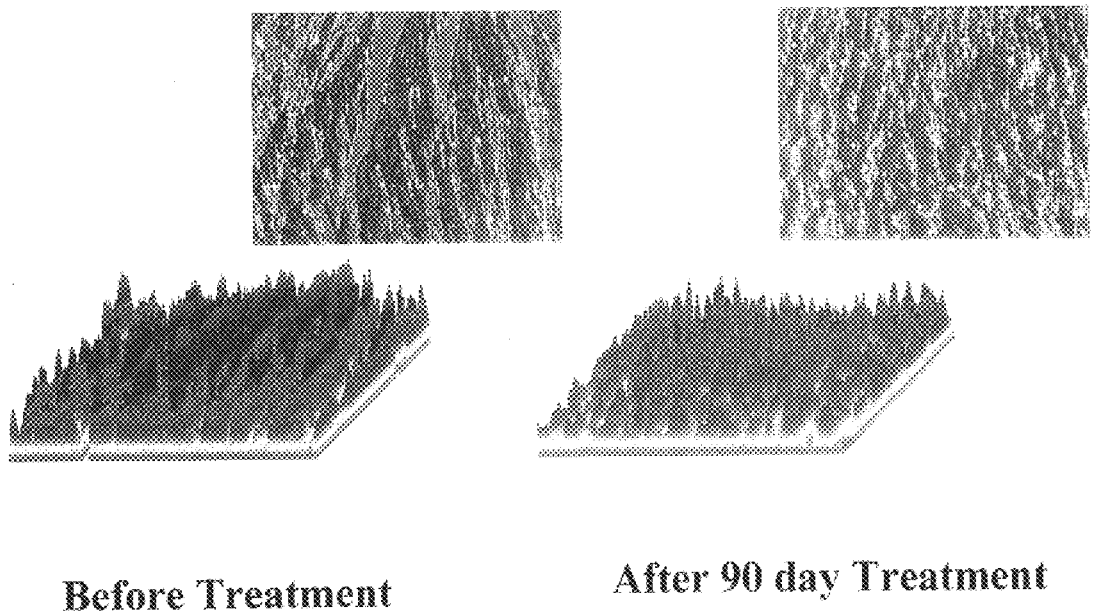

DELIVERY OF HYDROXY CARBOXYLIC ACIDS

CROSS REFERENCE TO RELATED APPLICATIONS

This is a divisional of application Ser. No. 09/148,675, filed Sep. 4, 1998, now allowed, which in turn is a continuation-in-part of application Ser. No. 09/041,173, filed Mar. 12, 1998, now abandoned.

FIELD OF THE INVENTION

The present invention relates to high purity bis(triorganosilyl)hydroxycarboxylic acid derivatives and a method for their preparation. More specifically, the present invention relates to more than 99% pure bis(triorganosilyl) hydroxycarboxylic acid derivatives prepared by triorganosilylation of hydroxycarboxylic acids by hexaorganodisilazanes. The present invention also relates to non-irritating cosmetic formulations comprising bis(triorganosilyl) hydroxycarboxylic acid derivatives.

BACKGROUND OF THE PRESENT INVENTION

There is considerable prior art relating to the use of hydroxycarboxylic acids, in particular alpha-hydroxycarboxylic acids such as glycolic acid and lactic acid, in skin care applications. Alpha-hydroxycarboxylic acids are basically used as chemical versions of facial scrubs. When applied topically, they accelerate the sloughing off of dead cells from the outer layer of the skin, the stratum corneum, forcing the underlying cells in the epidermis to accelerate the creation of fresh new cells to replace them. The body may also attempt to repair this minor damage, by depositing new collagen in the underlying dermal layer. The net apparent result is smoother, firmer, more evenly pigmented skin reminiscent of the person's skin at an earlier time chronologically. See generally, web page found at http://www.thriveonline.com/@@62AH9wYA2@Hgbb2a/thrive/health/skinsave.intro.html (Jul. 9, 1997 11:29 AM).

There are known side effects associated with the use, and in particular the prolonged use, of alpha-hydroxycarboxylic acids. These include acute skin irritation on application of the alpha-hydroxycarboxylic acid with possible development over time of an allergic-like reaction to such applications with some patients, and increased sun sensitivity.

Various techniques have been employed to decrease the side effects of alpha-hydroxycarboxylic acids such as partial neutralization, which increases the pH of the applied product (see Market View, The U.S. Cosmetics Industry, "Special Report, AHA Consumer Products 1990–1993," p.6.); partial or complete esterification, which also increases the pH of the applied product (see Genetic Engineering News dated Apr. 1, 1996 found at http://www.dc.enews.com/magazines/geng_news/archive/960401-005.html on Jul. 9, 1997); or the use of additives (see, Hahn, "A New Line of Defense Against Aging: Breaking the Irritation Barrier," DCI, January 1998). See also, generally, Parab, U.S. Pat. No. 5,420,105; Habif et al., U.S. Pat. No. 5,690,947; Hahn et al., U.S. Pat. No. 5,716,625; De Lacharriere et al., U.S. Pat. No. 5,714,155. None of these approaches change the real interaction of the alpha-hydroxycarboxylic acid with the epidermis. Rather, they provide the appearance of irritation reduction.

None of the current "solutions" to the irritation problem of alpha-hydroxycarboxylic acids has approached the problem by changing the delivery mechanism of the active ingredient such that it does not irritate the outer layers of the skin, yet the active ingredient targets the lipid-rich layers of the skin, more efficiently delivering free alpha-hydroxycarboxylic acid to those sites in the epidermis where the new cells are created.

Alpha-hydroxycarboxylic acid derivatives which have the ability to efficiently deliver free alpha-hydroxycarboxylic acids to preferred sites in the epidermis to promote new cell and collagen growth without irritation of the skin and with no associated toxicity concerns have clearly been sought for years to no avail. Associated with such a material would also be the desire for a simple high yield manufacturing process to make the material in the very high purity normally associated with cosmetic ingredients.

BRIEF DESCRIPTION OF THE DRAWINGS

The file of this patent contains at least one drawing executed in color.

FIG. 1 is a colored graphical depiction which shows the results of applying a lotion of the present invention in accordance with Example 7 to a 36 year old female patient who participated in the study of Example 7.

SUMMARY OF THE INVENTION

The present invention provides greater than 99% pure bis(triorganosilyl)hydroxy carboxylic acid derivatives of the general formulae:

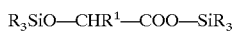

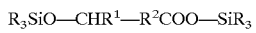

wherein each R is independently a monovalent straight or branched chain alkyl or alkenyl group having from 1 to about 6 carbon atoms, or an aryl group, $R^1$ may be hydrogen, a monovalent straight or branched chain alkyl group having from 1 to about 18 carbon atoms, or an aryl group, and $R^2$ is a divalent straight or branched chain alkyl group having from 1 to about 18 carbon atoms, an aryl group, or a straight or branched chain alkaryl group having from 7 to about 18 carbon atoms. The yield of bis(triorganosilyl)hydroxy carboxylic acid derivatives prepared by the method of the present invention is greater than about 95%.

The present invention also provides a simple method for rapidly producing bis(triorganosilyl)hydroxycarboxylic acid derivatives of the general formulae:

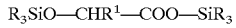

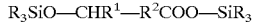

wherein each R is independently a monovalent straight or branched chain alkyl or alkenyl group having from 1 to about 6 carbon atoms, or an aryl group, $R^1$ may be hydrogen, a monovalent straight or branched chain alkyl group having from 1 to about 18 carbon atoms, or an aryl group, and $R^2$ is a divalent straight or branched chain alkyl group having from 1 to about 18 carbon atoms, an aryl group, or a straight or branched chain alkaryl group having from 7 to about 18 carbon atoms, the method comprising triorganosilylation with a hexaorganodisilazane of the corresponding hydroxy carboxylic acids of the general formulae:

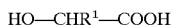

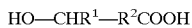

wherein $R^1$ may be hydrogen, a monovalent straight or branched chain alkyl group having from 1 to about 18 carbon atoms, or an aryl group, and $R^2$ is a divalent straight or branched chain alkyl group having from 1 to about 18 carbon atoms, an aryl group, or a straight or branched chain alkaryl group having from 7 to about 18 carbon atoms.

It has been found that bis(triorganosilyl) hydroxycarboxylate materials, which are aprotic, can be readily dissolved in typical aprotic solvents including organosilicone materials and can be delivered to the skin even under repeat insult conditions with no apparent irritation even under chronic use.

It is well known to those skilled in the art, that organosilicon chemicals containing silylether, Si—O—C, linkages and silylester, Si—O—C=O, linkages are hydrolytically unstable. In particular, silylester linkages are known to those skilled in the art to be more hydrolytically unstable than silylethers. Accordingly, bis(triorganosilyl) hydroxycarboxylates, on exposure to moisture, will undergo hydrolysis forming initially triorganosilylhydroxycarboxylic acids as per Equation 1.

$$R_3SiOCHR^1COOSiR_3 + H2O \rightarrow R_3SiOCHR^1COOH + R_3SiOH \quad (1)$$

Hydrolysis of both silylethers and silylesters is catalyzed by either acids or bases, thus although bis(triorganosilyl) hydroxy carboxylates are neutral, as they begin to hydrolyze they form carboxylic acids which catalyze further hydrolysis. Thus, the hydrolysis process is auto-catalytic. The second step of the hydrolysis process liberates free hydroxycarboxylic acid as per Equation 2.

$$R_3SiOCHR^1COOH + H2O \rightarrow HOCHR^1COOH + R_3SiOH \quad (2)$$

Bis(triorganosilyl)hydroxycarboxylates of the general formulae:

R$_3$SiO—CHR$^1$—COO—SiR$_3$

R$_3$SiO—CHR$^1$—R$^2$COO—SiR$_3$ wherein each R is independently a monovalent straight or branched chain alkyl or alkenyl group having from 1 to about 6 carbon atoms, or an aryl group, R$^1$ may be hydrogen, a monovalent straight or branched chain alkyl group having from 1 to about 18 carbon atoms, or an aryl group, and R$^2$ is a divalent straight or branched chain alkyl group having from 1 to about 18 carbon atoms, an aryl group, or a straight or branched chain alkaryl group having from 7 to about 18 carbon atoms, have the ability to deliver hydroxycarboxylic acids to the skin in such a manner as to not cause irritation or inflammation either acutely or chronically.

DETAILED DESCRIPTION OF THE INVENTION

The present invention provides greater than 99% pure bis(triorganosilyl)hydroxycarboxylic acid derivatives of the general formulae:

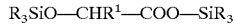

R$_3$SiO—CHR$^1$—COO—SiR$_3$

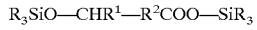

R$_3$SiO—CHR$^1$—R$^2$COO—SiR$_3$ wherein each R is independently a monovalent straight or branched chain alkyl or alkenyl group having from 1 to about 6 carbon atoms, or an aryl group, R$^1$ may be hydrogen, a monovalent straight or branched chain alkyl group having from 1 to about 18 carbon atoms, or an aryl group, and R$^2$ is a divalent straight or branched chain alkyl group having from 1 to about 18 carbon atoms, an aryl group, or a straight or branched chain alkaryl group having from 7 to about 18 carbon atoms.

The bis(triorganosilyl)hydroxy carboxylic acid derivatives of the present invention are prepared by triorganosilylation with a hexaorganodisilazane of the corresponding hydroxy carboxylic acids of the general formulae:

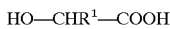

HO—CHR$^1$—COOH

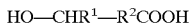

HO—CHR$^1$—R$^2$COOH wherein R$^1$ may be hydrogen, a monovalent straight or branched chain alkyl group having from 1 to about 18 carbon atoms, or an aryl group, and R$^2$ is a divalent straight or branched chain alkyl group having from 1 to about 18 carbon atoms, an aryl group, or a straight or branched chain alkaryl group having from 7 to about 18 carbon atoms.

Hydroxycarboxylic acids suitable for use in the process of the present invention, and methods for their preparation are well known to those skilled in the art. Specific examples include, but are not limited to, alpha-hydroxycarboxylic acids including glycolic acid and lactic acid, and beta-hydroxy-carboxylic acids including salicylic acid. The preferred hydroxy carboxylic acid is lactic acid.

Hexaorganodisilazanes suitable for use in the process of the present invention, and methods for their preparation are well known to those skilled in the art. Specific examples include, but are not limited to hexamethyldisilazane, hexaethyldisilazane, 1,3-divinyltetramethyldisilazane, and 1,3-diethyltetramethyldisilazane. The preferred hexaorganodisilazane is hexamethyldisilazane.

The triorganosilylation reaction may be carried out at temperatures ranging from about 40° C. to about 125° C., preferably between about 60° C. and about 95° C.

The compositions of the present invention are useful for all known utilities for topical administration of hydroxycarboxylic acids such as α-hydroxy acids and β-hydroxy acids. These include, for example, treatment of dry skin, xerosis, ichthyosis, dandruff, acne, keratoses, psoriasis, wrinkles, warts, blemished skin, hyperpigmented skin, inflammatory dermatoses, eczema, pruritis, hyperkerotic skin, lentigines, melasma, age spots, laxity, leathery texture, roughness, sallow complexion, scaling, telangiectasia, mottled pigmentation, skin atrophy caused by steroids and skin changes associated with intrinsic aging and photodamage.

In addition to the compositions of the present invention, the cosmetic formulations of the present invention may contain any of a large number of additional cosmetic and pharmaceutical agents, provided that such additional agents are inert with respect to formation, stability and activity of the compositions of the present invention, i.e., they are reaction inert. Additionally any such additives must be aprotic.

Cosmetic and pharmaceutical agents useful in the practice of the present invention include those that improve or eradicate age spots, keratoses and wrinkles, analgesics, anesthetics, antiacne agents, antibacterials, antiyeast agents, antifungal agents, antiviral agents, antidandruff agents, antidermatitis agents, antipruritic agents, antiinflammatory agents, antihyperkeratolytic agents, antidryskin agents, antiperspirants, antipsoriatic agents, antiseborrheic agents, hair conditioners, hair treatment agents, antiaging and antiwrinkile agents, antiphotoaging agents, antiasthmatic agents and bronchodilators, sunscreen agents, antihistamine agents, skin lightening agents, depigmenting agents, vitamins, corticosteroids, tanning agents, hormones, retinoids and topical cardiovascular agents.

The cosmetic formulation may be in the form that any aprotic formulation may take, including but not limited to lotions, creams, gels, sticks, ointments, liposomes, aerosols, polymeric gels, plasters, patches, films or tapes, the preparation of which are well known to those skilled in the art.

A neat bis(triorganosilyl)lactate can be applied to the skin with significantly less injury to the stratum corneum and epidermis than application of lactic acid at a similar aqueous concentration. Solutions of bis(triorganosilyl)lactate in aprotic vehicles at 10% effective lactic acid concentration (after hydrolysis), in the form of lotions or ointments, can be applied to the skin with no apparent acute or chronic irritation or inflammation.

DESCRIPTION OF THE PREFERRED EMBODIMENTS

The following examples illustrate the present invention. They are not to be construed to limit the scope of the appended claims in any manner whatsoever.

EXAMPLE 1

In a 3 liter 3-neck RB flask equipped with a magnetic stirring bar, a thermometer well and thermometer, addition funnel and heating mantle was placed 510 g (4.72 mole) of a 1:1 molar ratio of 83% wt/wt lactic acid in water. This liquid was heated and stirred to 60° C. To the addition funnel was added 1811 g (11.24 mole) of hexamethyldisilazane and the system was blanketed with a dry nitrogen atmosphere. Hexamethyldisilazane was then added slowly with stirring from the addition funnel to the lactic acid in water mixture, maintaining the temperature of the mixture at 60° C. Ammonia was liberated from the reaction medium and allowed to escape from the system through a bubbler. The addition of hexamethyldisilazane was continued overnight. After complete addition of the hexamethyldisilazane the mixture in the RB flask was heated at 80° C. for 4 more hours to ensure that the reaction had been driven to completion. A GC analysis of the crude product at this point showed the presence of three materials, hexamethyldisiloxane, hexamethyldisilazane and bis(trimethylsilyl)lactate in the approximate ratio of 35:15:50 respectively. The crude product was then fractionated producing 700 g (92% theory) of hexamethyldisiloxane, 95 g of a mixture of hexamethyldisiloxane and hexamethyldisilazane, 260 g (90% theory) of unreacted hexamethyldisilazane. At this point the remaining liquid was cooled to room temperature, a full vacuum was applied and the product was distilled at 1 mm of Hg pressure at a temperature of 40° C. to provide 1050 g (95% yield) of >99.9% pure (by GC analysis) clear, colorless and odorless bis(trimethylsilyl)lactate, refractive index 1.4053 (21° C.) and density 0.896 (21° C.). A GC/MS analysis of this material identified the molecular weight of the chemical to be 234.

EXAMPLE 2

In a 250 ml 3-neck RB flask equipped with a magnetic stirring bar, a thermometer well and thermometer, a powder addition funnel and heating mantle was placed 106 g (0.66 mole) of hexamethyldisilazane. This liquid was heated and stirred to 60° C. To the powder addition funnel was added 45 g (0.59 mole) of solid glycolic acid and the system was blanketed with a dry nitrogen atmosphere. Solid glycolic acid was then added slowly with stirring from the addition funnel to the hexamethyldisilazane, maintaining the temperature of the mixture at 60° C. Ammonia was liberated from the reaction medium and allowed to escape from the system through a bubbler. The addition was completed in 4 hours. After complete addition of the glycolic acid the mixture in the RB flask was heated at 80° C. for 4 more hours to ensure that the reaction had been driven to completion. A GC analysis of the crude product at this point showed the presence of two materials, hexamethyldisilazane and bis(trimethylsilyl)-glycolate in the approximate ratio of 10:90 respectively. The crude product was then stripped to remove the excess hexamethyldisilazane leaving the product which was distilled at a temperature of 45° C. at a vacuum of 1 mm of Hg to provide 120 g (95% yield) of 100% pure (by GC analysis) clear, colorless and odorless bis(trimethylsilyl)glycolate, refractive index 1.4119 (21° C.) and density 0.905 (21° C.). A GC/MS analysis of this material identified the molecular weight of the chemical to be 220.

EXAMPLE 3

In a 250 ml 3-neck RB flask equipped with a magnetic stirring bar, a thermometer well and thermometer, a powder addition funnel and heating mantle was placed 59 g (0.37 mole) of hexamethyldisilazane. This liquid was heated and stirred to 60° C. To the powder addition funnel was added 45 g (0.29 mole) of solid salicylic acid and the system was blanketed with a dry nitrogen atmosphere. Solid salicylic acid was then added slowly with stirring from the addition funnel to the hexamethyl-disilazane, maintaining the temperature of the mixture at 60° C. Ammonia was liberated from the reaction medium and allowed to escape from the system through a bubbler. The addition was completed in 4 hours. After complete addition of the salicylic acid the mixture in the RB flask was heated at 80° C. for 4 more hours to ensure that the reaction had been driven to completion. A GC analysis of the crude product at this point showed the presence of two materials, hexamethyldisilazane and bis(trimethylsilyl)salicylate in the approximate ratio of 25:75 respectively. The crude product was then stripped to remove the excess hexamethyldisilazane leaving the product which was distilled at a temperature of 78° C. at a vacuum of 1 mm of Hg to provide 77 g (95% yield) of 100% pure (by GC analysis) clear, colorless and odorless bis(trimethylsilyl)salicylate, refractive index 1.4788 (21° C.) and density 0.99 (21° C.). A GC/MS analysis of this material identified the molecular weight of the chemical to be 282.

EXAMPLE 4

Primary skin irritation studies in rabbits of undiluted bis(trimethylsilyl)lactate was evaluated by Hill Top Research, Inc. (Project No. 97-8487-21) in compliance with the conditions specified in the regulation for the enforcement of the Federal Hazardous Substances Act (16 C.F.R. §1500). The test material produced moderate to severe erythema and severe edema (raised more than 1 mm and extending beyond the area of exposure) when applied to one intact and one abraded skin site on each of six rabbits. Additional changes noted in the coloration or texture of the skin included purple, light brown, green and green-brown discoloration on and extending beyond sites; in-depth blanching on site; blanching on and extending beyond site; and site and areas beyond site coriaceous. The Primary Irritation Index (PII) was found to be 7.1 based upon erythema and edema. Evidence of corrosion (in-depth blanching) was noted at an intact and abraded site at the 72 hour reading. Undiluted bis(trimethylsilyl)lactate is classified as a primary irritant but not as a corrosive based upon the response observed following dermal application.

For comparison, a solution of 85% lactic acid in water is classified as corrosive and causes burns. Suitable protective clothing includes heavy rubber gloves and eye and face protection. (Reference: MSDS from Aldrich Chemical Company, Inc., P.O. Box 355, Milwaukee, Wis. 53201, USA)

EXAMPLE 5

Facial Sensitivity studies in humans were carried out by Hill Top Research, Inc. (Project Nos. 97-2809-72 and 100969-72). The studies followed a double-blinded paired comparison design of 10% (w/w) lactic acid in water, 25% bis(trimethylsilyl)lactate) in Phenyl Trimethicone, 25% bistrimethylsilyl)glycolate in Phenyl Trimethicone, 20% bis (trimethylsilyl)salicylate in Phenyl Trimethicone, Phenyl Trimethicone and water. The objective of the studies was to compare the stinging potential of the three trimethylsilylated hydroxyacid derivatives in an anhydrous delivery vehicle to that of the standard water-based chemical probe under supervised, time application procedures. Thirty female subjects, prequalified as "stingers" to 10% lactic acid, completed the studies where the test samples were applied to the nasolabial fold. Only three of the thirty subjects demonstrated a mild sting response. There were no adverse events associated with the use of the test articles.

EXAMPLE 6

Anhydrous lotion and anhydrous ointment formulations have been developed containing 25% (w/w) bis (trimethylsilyl)lactate as the active ingredient for chronic exposure and efficacy testing. This concentration corresponds to 10% lactic acid upon exposure of the formulations to water and complete hydrolysis of the bis(trimethylsilyl) lactate.

The compositions of the formulations are as follows:

| Lotion: | 3-n-Hexylheptamethyltrisiloxane | 50% |
|---|---|---|
| | Bis(trimethylsilyl) lactate | 25% |
| | Dimethiconol (HMW) | 18% |
| | Polybutene | 4% |
| | Caprylyl Trimethicone | 2% |
| | Pareth-15 | 0.5% |
| | Fragrance | 0.5% |
| Ointment: | Bis(trimethylsilyl)lactate | 25% |
| | C24-28 Alkylmethylsiloxane Wax | 24.5% |
| | Caprylic/Capric/Stearic Triglycerides | 25% |
| | 3-n-Hexylheptamethyltrisiloxane | 20% |
| | Caprylic/Capric Triglycerides | 3% |
| | Caprylyl Trimethicone | 2% |
| | Fragrance | 0.5% |

Repeat insult daily topical application to human skin of both the lotion and the ointment was carried out for 30 days (60 applications on the inside of the forearm and on the back of the hand). No acute reactions to these formulations were observed or felt during this period and no indications of sensitization to the formulations were observed.

EXAMPLE 7

The anhydrous lotion and anhydrous ointment formulations described in Example 6 were utilized in a comprehensive efficacy testing program conducted by Hill Top Research, Inc. A lotion and an ointment containing the same ingredients as described above, except without the active, bis(trimethylsilyl)lactate were also prepared. An efficacy study of the four formulations, using over 100 women, of ages ranging from 30 to 60 years, was conducted over a 90 day period. The group was divided into approximately 35 with the active lotion, 17 with the inactive lotion, 35 with the active ointment and 17 with the inactive ointment. Participants were requested to apply their test material to the face twice daily. Visual analysis of participants was conducted at the beginning, and weeks 2, 4, 8 and 12. A trained dermatologist supervised these analyses. Silicone negative facial skin replicates were made of all participants at the beginning, and weeks 4 and 12. Quantitative analysis of the skin replicates was obtained by laser light scanning directed at a 25° angle from the plane of the replica. A Cohu Solid State B&W camera was used to photograph each of the scans. The B&W luminance pattern of each scan was then converted into a visible color image of each replica. Changes in the skin surface during the 90 day efficacy test are readily seen via these color images. Standard statistical methods were used to analyze all of the data obtained in this study.

Twenty nine within treatment study parameters and fifteen between treatment study parameters were determined to be statistically significant. These include reductions in fine lines, coarse wrinkling, mean spacing of lines, tactile roughness, mottled pigmentation, yellowing, and erythema. Reduction in the % of the negative skin replicate area covered by shadows was statistically significant. Table I lists all of the study parameters which were identified to have undergone statistically significant change. FIG. 1 shows the results in color of one of the 36 year old female patients treated with a lotion with the active ingredient.

TABLE I

Statistically Significant Study Parameter Changes

Study Parameter
(Within Treatment)

| | |
|---|---|
| % Area Covered by Shadow | Cream w/ Active vs. Baseline at Week 4 |
| % Area Covered by Shadow | Gel w/ Active vs. Baseline at Week 12 |
| Fine Lines | Cream Base vs. Baseline at Weeks 2/8 |
| Fine Lines | Cream w/ Active vs. Baseline at Weeks 2/4/8/12 |
| Fine Lines | Gel Base vs. Baseline at Week 8 |
| Fine Lines | Gel w/ Active vs. Baseline at Weeks 2/4/8/12 |
| Coarse Wrinkling | Cream w/ Active vs. Baseline at Weeks 2/8/12 |
| Coarse Wrinkling | Gel w/ Active vs. Baseline at Weeks 2/8 |
| Normal A Roughness | Cream W/ Active vs. Baseline at Weeks 4/12 |
| Normal A Roughness | Gel w/ Active vs. Baseline at Weeks 4/12 |
| Normal Z Roughness | Cream w/ Active vs. Baseline at Weeks 4/12 |
| Normal Z Roughness | Gel w/ Active vs. Baseline at Weeks 4/12 |
| Tactile Roughness | Cream Base vs. Baseline at Week 8 |
| Tactile Roughness | Cream w/ Active vs. Baseline at Week 8 |
| Tactile Roughness | Gel Base vs. Baseline at Week 8 |
| Tactile Roughness | Gel w/ Active vs. Baseline at Week 8 |
| Erythema | Cream Base vs. Baseline at Weeks 2/4/8/12 |
| Erythema | Cream w/ Active vs. Baseline at Weeks 2/4/8/12 |
| Mottled Pigmentation | Cream Base vs. Baseline at Weeks 2/4/8/12 |
| Mottled Pigmentation | Cream w/ Active vs. Baseline at Weeks 2/4/8/12 |
| Mottled Pigmentation | Gel Base vs. Baseline at Weeks 2/4/8/12 |
| Mottled Pigmentation | Gel w/ Active vs. Baseline at Weeks 2/4/8/12 |
| Yellowing | Cream Base vs. Baseline at Weeks 2/4/8/12 |

TABLE I-continued

Statistically Significant Study Parameter Changes

| | |
|---|---|
| Yellowing | Cream w/ Active vs. Baseline at Weeks 2/4/8/12 |
| Yellowing | Gel Base vs. Baseline at Weeks 2/4/8/12 |
| Yellowing | Gel w/ Active vs. Baseline at Weeks 2/4/8/12 |
| Stinging | Cream w/ Active vs. Baseline at Week 2 only |
| Stinging | Gel w/ Active vs. Baseline at Week 2 only |
| Study Parameter (Between Treatments) | |
| % Area Covered by Shadow | Cream w/ Active vs. Cream Base |
| Fine Lines | Cream w/ Activs va. Cream Base at Weeks 8/12 |
| Fine Lines | Gel w/ Active vs. Gel Base at Weeks 8/12 |
| Coarse Wrinkling | Cream w/ Active vs. Cream Base at Weeks 8/12 |
| Coarse Wrinkling | Gel w/ Active vs. Gel Base Overall |
| Coarse Wrinkling | Cream w/ Active vs. Gel w/ Active Overall |
| Mean Wrinkle Spacing | Gel w/ Active vs. Gel Base at Week 4 |
| Tactile Roughness | Cream w/ Active vs. Cream Base Overall |
| Tactile Roughness | Gel w/ Active vs. Gel Base Overall |
| Erythema | Cream w/ Active vs. Cream Base Overall |
| Erythema | Gel w/ Active vs. Gel Base Overall |
| Mottled Pigmentation | Cream w/ Active vs. Gel w/ Active Overall |
| Yellowing | Cream w/ Active vs. Cream Base Overall |
| Yellowing | Gel w/ Active vs. Gel Base Overall |
| Stinging | Gel w/ Active vs. Gel Base at Week 2 only |

Variations of the present invention will suggest themselves to those skilled in the art in light of the above detailed description. For example, a mixture of hydroxy carboxylic acids could be triorganosilylated to produce a mixture of Bis(triorganosilyl)hydroxycarboxylic acid derivatives. Similarly, a mixture of hexaorganodisilazanes can be used to produce a mixture of bis(triorganosilyl)hydroxycarboxylic acid derivatives. All such modifications are within the full intended scope of the appended claims.

All of the above-referenced patents and publications are hereby incorporated by reference.

What is claimed is:

1. A method of delivering a hydroxycarboxylic acid to the epidermis without apparent corrosion or burning of the epidermis or stratum corneum, said method comprising applying a cosmetic formulation comprising a bis(triorganosilyl)hydroxycarboxylate in an aprotic media to the epidermis.

2. A method as defined in claim 1 wherein statistically significant reductions of one or more of fine lines, coarse wrinkling, roughness, erythema, mottled pigmentation and yellowing are obtained within a twelve week period.

3. A method as defined in claim 1 wherein said bis(triorganosilyl)hydroxycarboxylate comprises a compound of the general formulae

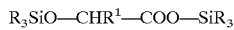

$R_3SiO\text{—}CHR^1\text{—}COO\text{—}SiR_3$

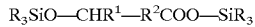

$R_3SiO\text{—}CHR^1\text{—}R^2COO\text{—}SiR_3$ wherein each R is independently a monovalent straight or branched chain alkyl or alkenyl group having from 1 to about 6 carbon atoms, or an aryl group, $R^1$ is hydrogen, a monovalent straight or branched chain alkyl group having from 1 to about 18 carbon atoms, or an aryl group, $R^2$ is a divalent straight or branched chain alkyl group having from 1 to about 18 carbon atoms, an aryl group, or a straight or branched chain alkaryl group having from 7 to about 18 carbon atoms.

4. A method as defined in claim 3 wherein said bis(triorganosilyl)hydroxycarboxylate is selected from the group consisting of bis(trimethylsilyl)-glycolate, bis(trimethylsilyl)lactate, bis(trimethylsilyl)-salicylate and mixtures of any of the foregoing.

5. A method as defined in claim 3 wherein said bis(triorganosilyl)hydroxycarboxylate is at least about 99% pure.

6. A method as defined in claim 1 wherein said aprotic media is selected from the group consisting of dimethicones, cyclomethicones, alkyl methicones, alkyl dimethicones, alkyl trimethicones, aryl trimethicones, polybutenes, acyl triglycerides and mixtures of any of the foregoing.

7. A method as defined in claim 1 wherein said bis(triorganosilyl)hydroxycarboxylate is dissolved in said aprotic media at from about 10 to about 40% (w/w).

8. A method as defined in claim 7 wherein said bis(triorganosilyl)hydroxycarboxylate is dissolved in said aprotic media at about 25% (w/w).

9. A method as defined in claim 3 wherein said hydroxycarboxylic acid is of the general formulae:

$HO\text{—}CHR^1\text{—}COOH$

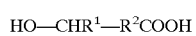

$HO\text{—}CHR^1\text{—}R^2COOH$ wherein $R^1$ is hydrogen, a monovalent straight or branched chain alkyl group having from 1 to about 18 carbon atoms, or an aryl group, and $R^2$ is a divalent straight or branched chain alkyl group having from 1 to about 18 carbon atoms, an aryl group, or a straight or branched chain alkaryl group having from 7 to about 18 carbon atoms.

* * * * *